(12) United States Patent
El-Fahmawi

(10) Patent No.: US 11,660,078 B2
(45) Date of Patent: May 30, 2023

(54) SAMPLE COLLECTION DEVICE

(71) Applicant: MAWI DNA TECHNOLOGIES LLC, Hayward, CA (US)

(72) Inventor: Bassam El-Fahmawi, Hayward, CA (US)

(73) Assignee: MAWI DNA TECHNOLOGIES LLC, Hayward, CA (US)

(*) Notice: Subject to any disclaimer, the term of this patent is extended or adjusted under 35 U.S.C. 154(b) by 1091 days.

(21) Appl. No.: 16/308,616

(22) PCT Filed: Aug. 10, 2017

(86) PCT No.: PCT/US2017/046374
§ 371 (c)(1),
(2) Date: Dec. 10, 2018

(87) PCT Pub. No.: WO2018/031824
PCT Pub. Date: Feb. 15, 2018

(65) Prior Publication Data
US 2020/0305850 A1 Oct. 1, 2020

Related U.S. Application Data

(60) Provisional application No. 62/373,255, filed on Aug. 10, 2016.

(51) Int. Cl.
*A61B 10/00* (2006.01)
*B01L 3/00* (2006.01)

(52) U.S. Cl.
CPC ........ *A61B 10/0051* (2013.01); *B01L 3/5082* (2013.01); *B01L 2200/12* (2013.01);
(Continued)

(58) Field of Classification Search
CPC ............... A61B 10/0051; B01L 3/5082; B01L 2200/12; B01L 2300/0681;
(Continued)

(56) References Cited

U.S. PATENT DOCUMENTS 3,880,591 A * 4/1975 Burroughs ......... G01N 33/4972
600/529
4,283,498 A 8/1981 Schlesinger
(Continued)

FOREIGN PATENT DOCUMENTS

EP 1051616 A2 11/2000
WO 2015198031 A1 12/2015

OTHER PUBLICATIONS

European Patent Office Examination Report for Application No. 17840309.3 dated Feb. 22, 2021 (5 pages).
(Continued)

*Primary Examiner* — Matthew D Krcha
*Assistant Examiner* — Jacqueline Brazin
(74) *Attorney, Agent, or Firm* — Michael Best & Friedrich LLP

(57) ABSTRACT

A sample collection device including a collection tube at least partially defining a storage volume therein, a mouthpiece coupled to the collection tube, the mouthpiece defining a channel providing access to the storage volume, and a filter at least partially positioned within the channel, where the filter is configured to filter a sample as it passes through the channel and into the storage volume.

35 Claims, 9 Drawing Sheets

(52) U.S. Cl.
CPC ............... *B01L 2300/0681* (2013.01); *B01L 2300/0832* (2013.01); *B01L 2300/0848* (2013.01)

(58) Field of Classification Search
CPC .... B01L 2300/0832; B01L 2300/0848; C12M 3/06; C12M 1/40; C12M 3/00
USPC ........................................................ 600/576
See application file for complete search history.

(56) References Cited

U.S. PATENT DOCUMENTS

| | | | | |
|---|---|---|---|---|
| 4,942,887 | A * | 7/1990 | Abdelgawad | A24D 3/043 131/339 |
| 6,389,609 | B1 | 5/2002 | Andritz | |
| 6,416,715 | B1 * | 7/2002 | Gambert | A61B 10/0051 422/513 |
| 2010/0102002 | A1 | 4/2010 | O'Brien et al. | |
| 2010/0331725 | A1 * | 12/2010 | Libby | A61B 10/0051 600/573 |
| 2012/0046574 | A1 * | 2/2012 | Skakoon | A61B 10/0051 600/576 |
| 2014/0008210 | A1 * | 1/2014 | Guia | G01N 33/491 204/518 |

OTHER PUBLICATIONS

European Patent Office Examination Report for Application No. 17840309.3 dated Sep. 1, 2021 (5 pages).
International Search Report and Written Opinion for PCT Application No. PCT/US2017/046374 dated Oct. 19, 2017 (7 pages).
International Preliminary Report on Patentability for PCT Application No. PCT/US2017/046374 dated Feb. 21, 2019 (7 pages).
Extended European Search Report from the European Patent Office for Application No. 17840309.3 dated Feb. 13, 2020 (8 pages).

* cited by examiner

SAMPLE COLLECTION DEVICE

CROSS-REFERENCE TO RELATED APPLICATION(S)

This patent application is a U.S. national stage entry of International Patent Application No. PCT/US2017/046374, filed on Aug. 10, 2017, which claims priority to U.S. Provisional Patent Application No. 62/373,255, filed on Aug. 10, 2016, the entire contents of each of which are fully incorporated herein by reference.

FIELD OF THE INVENTION

The embodiments described here relate to the collection of biological samples, and more particularly, to a particle filtering and shredding device for oral sample collection.

BACKGROUND OF THE INVENTION

Oral cavity content, such as saliva, sputum, or buccal cells, can provide an immense amount of information about our health and is a viable alternative for a blood sample. Oral sampling is quite appealing due to its non-invasive nature and can be self-collected with limited assistance.

A variety of advancement has been achieved to simplify oral sample collection for DNA/analyte stabilization and transport at room temperature. Oral sample collection is conventionally achieved using one of two methods—either intra-orally or by soaking a swab or sponge and then either releasing it into a collection device with stabilizer or the analyte stabilizer is added later by the collector.

Direct spit into a tube with or without a funnel is another approach for self-collection or oral samples. Several innovations have been introduced to help stabilize the collected sample at the point of collection, the most popular being to include the stabilizing buffer in the film covered cap/lid, which breaks when it comes in contact with a piercing protrusion in the lid receiving end and then releases the stabilized content to mix with the collected oral sample. Alternatively, the stabilizing buffer may be either dried inside the sample collection tube or provided separately in an ampule for the collector to break open and dispense the content to mix with the collected oral sample for optimized stabilization of the collected sample.

While methods and devices exist for collecting and stabilizing oral samples, none of the existing methods or devices addresses the issues that collecting a 1-2 mL sample size may be very challenging, especially for young children or the elderly. Moreover, the conventional devices collect samples that often contain food particles and other contaminants, which (1) increases bacterial content and thus lowers the quality of the DNA downstream applications; (2) can clog pipette tips during sample processing, resulting in sample failure; (3) adds a centrifugation step prior to processing the sample to eliminate the food particles, increasing turnaround time and reducing sample processing efficiency; and (4) reduces the gDNA stability overtime.

SUMMARY OF THE INVENTION

In one embodiment, the invention provides a sample collection device including a collection tube at least partially defining a storage volume therein, a mouthpiece coupled to the collection tube, the mouthpiece defining a channel providing access to the storage volume, and a filter at least partially positioned within the channel, where the filter is configured to filter a sample as it passes through the channel and into the storage volume.

In another embodiment, the invention provides a filtering device for use with a collection tube defining a storage volume therein, the filtering device including a mouthpiece that is substantially conical in shape and defining a channel configured to allow a sample to flow therethrough, and a filter at least partially positioned within the channel, where the filter defines a plurality of apertures configured to filter a sample passing through the channel.

In yet another embodiment, the invention provides a filtering device for use with a collection tube defining a storage volume therein, the filtering device including a channel having a first end and a second end opposite the first end, a mouthpiece extending from the channel proximate the first end, where the mouthpiece is substantially conical in shape, and a perforated wall enclosing the second end of the channel, where the perforated wall defines a plurality of apertures therein.

Other aspects of the invention will become apparent by consideration of the detailed description and accompanying drawings.

DETAILED DESCRIPTION

Figure 1:
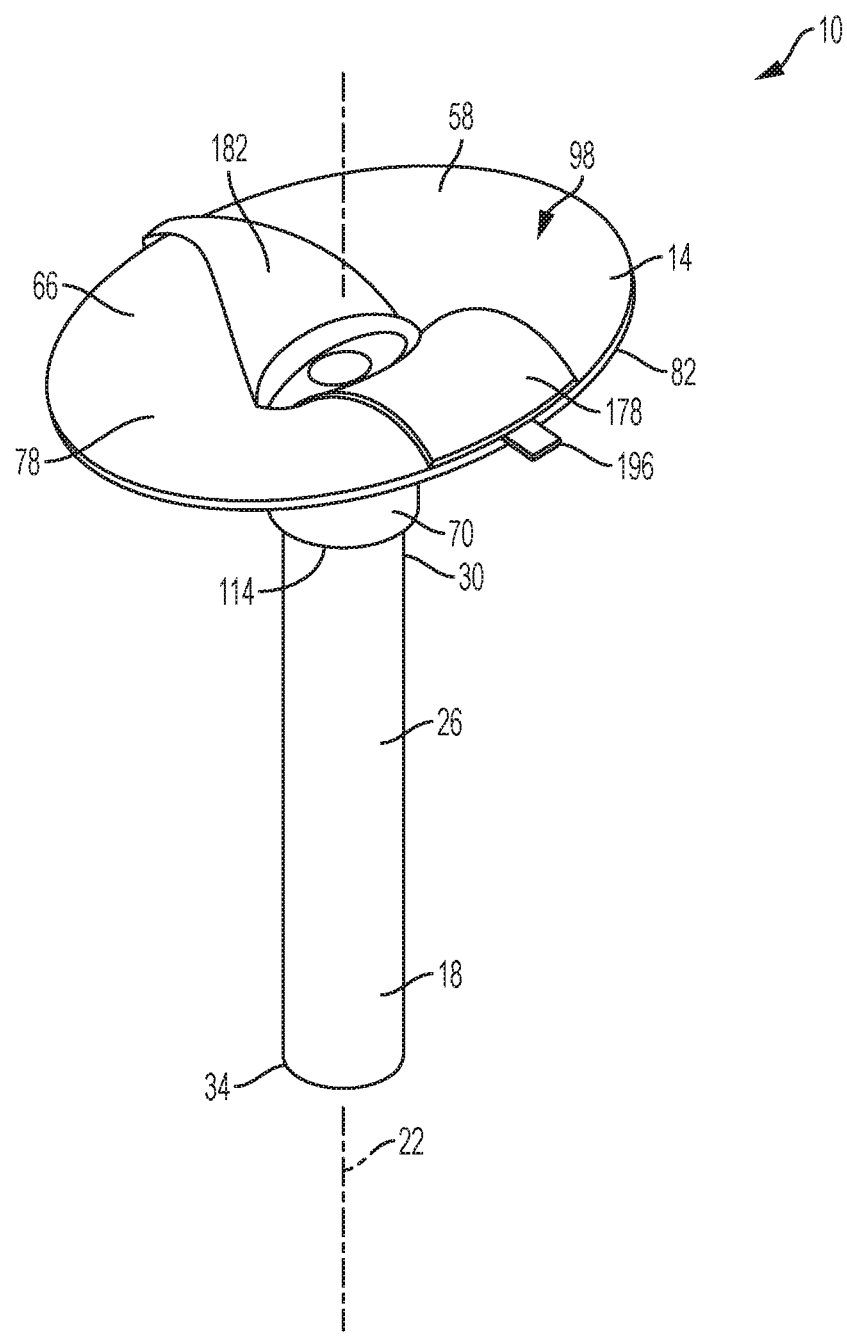
FIG. 1 illustrates a sample collection device of the present invention with the lid in the closed position.
Figure 2:
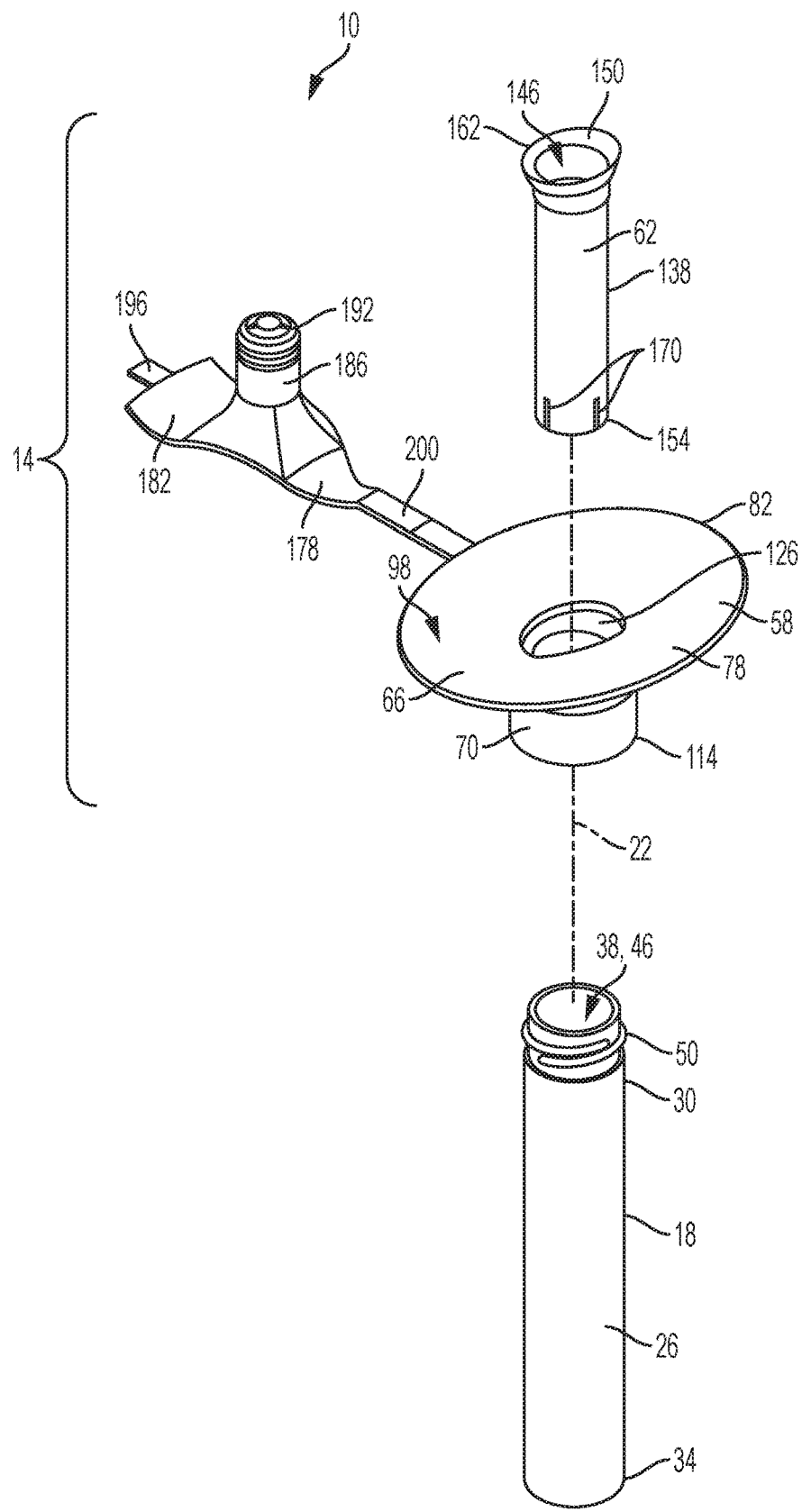
FIG. 2 illustrates an exploded view of the sample collection device of FIG. 1.
Figure 3:
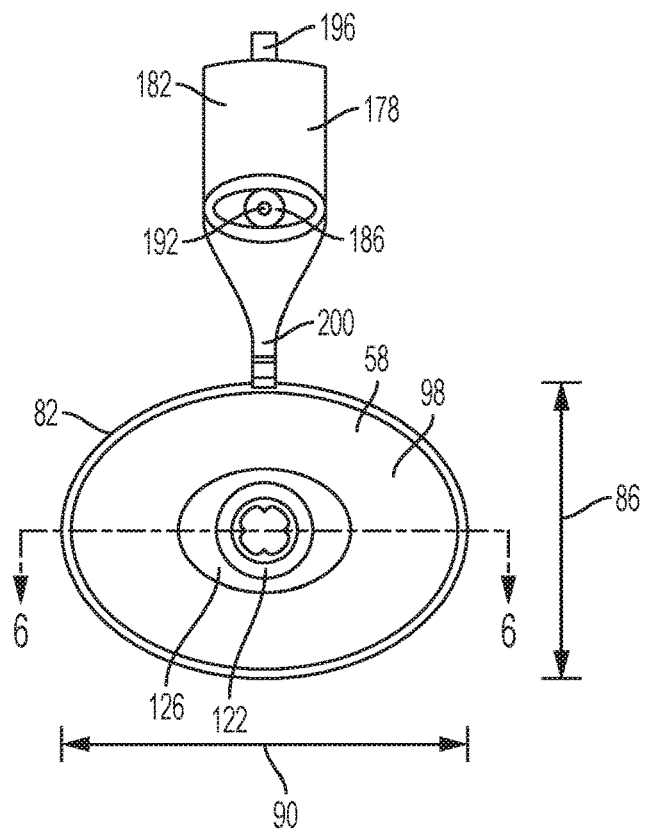
FIG. 3 is a top view of the sample collection device of FIG. 1 with the lid in the open position.
Figure 4:
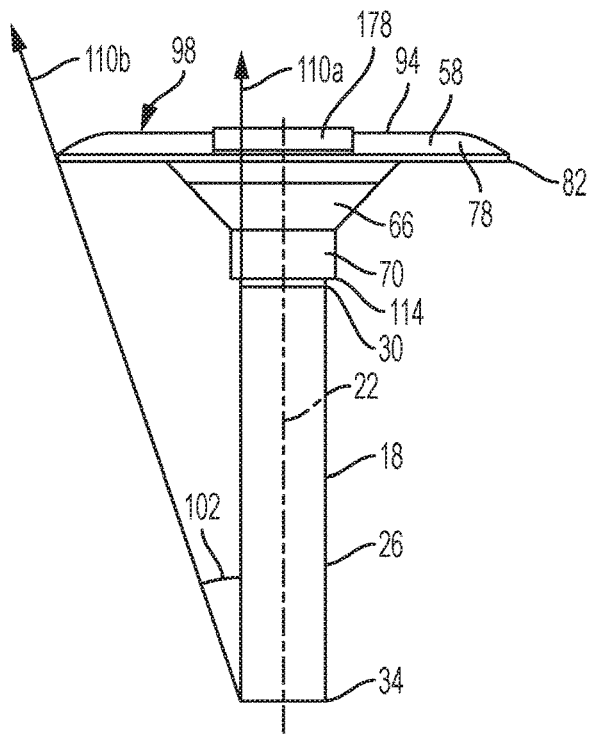
FIG. 4 is a front view of the sample collection device of FIG. 1 with the lid in a closed position.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

FIGS. 1-6 and 8-12 illustrate a sample collection device 10 for collecting, filtering, and stabilizing an oral sample such as saliva, sputum, buccal cells, and the like. The collection device 10 includes a filtering device 14 to collect and filter the sample, and a collection tube 18 where the sample is mixed with a stabilizing buffer and stored for subsequent use. During operation, the sample passes through the filtering device 14 where particulates and other debris (e.g., food particles and the like) are removed from the sample. The sample is subsequently deposited within the collection tube 18 where the sample is mixed with a volume of stabilizing buffer for long-term storage. In the illustrated embodiment, the filtering device 14 may also aid in the stabilization process by helping to mix the sample with the stabilizing buffer. Furthermore, while the filtering device 14 and collection tube 18 are shown and described as a single unit, it is to be understood that the filtering device 14 is self-contained and may be retro-fit onto existing collection tubes 18 to provide the necessary filtering, shredding, and mixing characteristics described below. Still further, while the present invention is discussed in view of the collection and processing of an oral sample, it is to be understood that the sample collection device may be used to collect any biological sample, such as but not limited to, stool, urine, blood, sweat, tissue, semen, and the like.

Illustrated in FIGS. 1-4, and 6, the collection tube 18 of the sample collection device 10 is substantially cylindrical in shape defining an axis 22 extending therethrough. The collection tube 18 includes an outer annular wall 26 that has a first end 30, and a second end 34 opposite the first end 30. The annular wall 26 also defines a channel 38, which in turn, is subdivided by a dividing wall 42 positioned axially between the first end 30 and the second end 34. Together, the annular wall 26 and the dividing wall 42 at least partially define a storage volume 46 in which the sample can be stored. In the illustrated embodiment, the dividing wall 42 is positioned approximately midway between the first and second ends 30, 34; however, in alternative embodiments the position of the dividing wall 42 may be altered to change the capacity of the storage volume 46 as necessary.

The first end 30 of the collection tube 18 includes a set of external threads 50 and provides access to the storage volume 46 of the collection tube 18. The external threads 50 of the first end 30 are sized to threadably engage both the internal threads of filtering device 14 (described below) and the internal threads of a travel cap 54 (described below). Although not shown, the first end 30 of the collection tube 18 may also include a gasket or other sealing device to form a seal with at least one of the filtering device 14 or the travel cap 54.

Illustrated in FIGS. 1-7, the filtering device 14 of the sample collection device 10 includes a mouthpiece or collection top 58, and a filter 62 removably coupled to the mouthpiece 58. During use, the filtering device 14 is threadably coupled to and forms a seal with the first end 30 of the collection tube 18 such that the sample must pass through the filtering device 14 in order to enter the storage volume 46 of the collection tube 18. The filtering device 14 is configured to collect and filter the sample as it passes therethrough so that resulting sample positioned within the storage volume 46 is substantially free of debris and food particles.

Illustrated in FIGS. 1-4, and 6-12, the mouthpiece 58 of the filtering device 14 is generally conical in shape having a body 66 with a neck portion 70 defining a channel 74, and a flange portion 78 extending radially outwardly from the neck portion 70 to form an outer perimeter 82. During use, the mouthpiece 58 acts as a funnel providing an outer surface 98 or interface against which the user can place his or her mouth and that directs the sample toward the channel 74 and into the filter 62 positioned therein (described below).

In the illustrated embodiment, the flange portion 78 of the mouthpiece 58 includes an oval-shaped outer perimeter 82 having a height 86 and width 90 substantially corresponding to but sized larger than the height and width of a human mouth. The flange portion 78 also forms a smooth convex shape such that the forward most point 94 of the outer surface 98 of the flange portion 78 is positioned axially forward of the outer perimeter 82 (see FIG. 4). In all, the flange portion 78 of the body 66 is configured to ergonomically conform to the user's lips such that a "spitting action" results in the sample being directed toward the channel 74 and into the filter 62 with limited spillage or spatter.

Furthermore, the height 86 and width 90 of the outer perimeter 82 is sufficiently large so that, when the mouthpiece 58 is coupled to the collection tube 18, the resulting device 10 forms a "rest angle 102" sufficiently large to limit the volume of sample that can exit the storage volume 46 when the device 10 is knocked or tipped over (e.g., rotates from a substantially vertical orientation to a substantially horizontal orientation). Stated differently, the rest angle 102 represents the angle at which the device 10 will rest on a support surface in a substantially horizontal orientation (see FIG. 4). In the illustrated embodiment, the rest angle 102 is large enough so that at least a portion of the open end 150 of the filter 62 is positioned vertically above the perforated wall 158 when the device 10 is positioned on a support surface.

For the purposes of this application, the rest angle 102 of the collection device 10 is defined as the angle formed between two rays 110a, 110b positioned on a single plane that passes through the axis 22. More specifically, the first ray 110a originates at the second end 34 of the collection tube 18 and extends axially along the annular wall 26, while the second ray 110b originates at the same point as the first ray 110a and extends outwardly such that it intersects with the outer perimeter 82 of the mouthpiece 58 (see FIG. 4). In the present embodiment, the outer perimeter 82 is non-circular and therefore the rest angle 102 varies dependent upon the orientation at which the device 10 is positioned on the support surface. In such embodiments, the smallest rest angle 102 that can result is regarded as the minimum rest angle. In the illustrated embodiment, the minimum rest angle 102 is greater than approximately 10 degrees. In other embodiments, the rest angle 102 may be between approximately 5 degrees and approximately 45 degrees. In still other embodiments, the rest angle 102 may be between approximately 8 degrees and approximately 30 degrees. In still other embodiments, the rest angle 102 may be between 10 degrees and approximately 20 degrees.

The neck 70 of the mouthpiece 58 is substantially annular in shape having a distal end 114 and at least partially defining the channel 74 sized to allow at least a portion of the filter 62 to be positioned therein. The channel 74 includes a first or threaded portion 122 positioned proximate the distal end 114, and a second portion 126 extending from the threaded portion 122 away from the distal end 114. In the illustrated embodiment, the threaded portion 122 of the channel 74 includes a set of internal threads 130 that are sized to threadably engage the external threads 50 of the first end 30 of the collection tube 18.

The second portion 126 of the channel 74 is sized and shaped to correspond with the exterior profile of the open end 150 of the filter 62 (described below). More specifically, the second portion 126 is configured to engage the open end 150 of the filter 62 and restrict the axial movement of the open end 150 through the channel 74. In some embodiments, the second portion 126 may also include a gasket or other elements such that a seal is formed between the second portion 126 and the open end 150.

Figure 5:
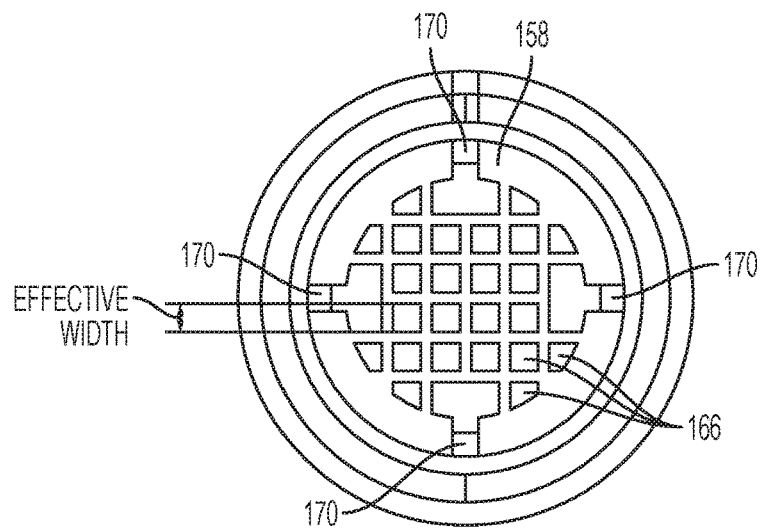
FIG. 5 is a detailed view of the perforated wall of the sample collection device of FIG. 1.
Figure 6:
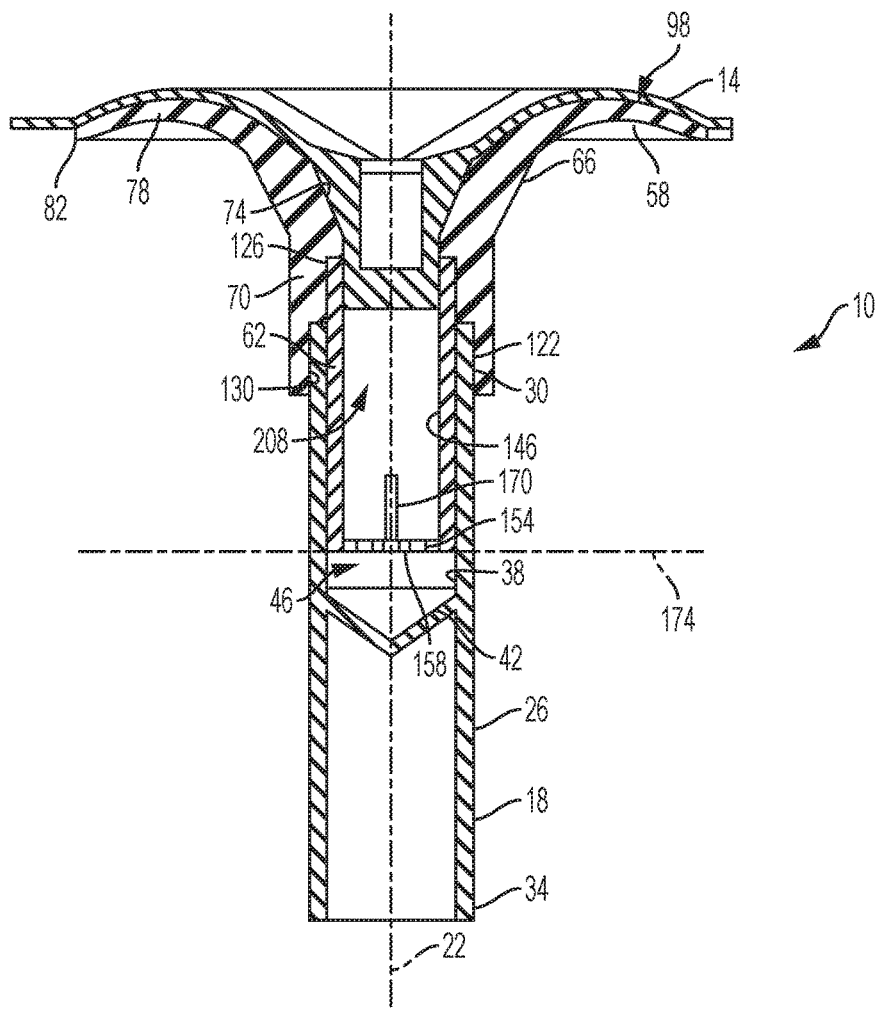
FIG. 6 is a section view take along line 6-6 of FIG. 3.
Figure 7:
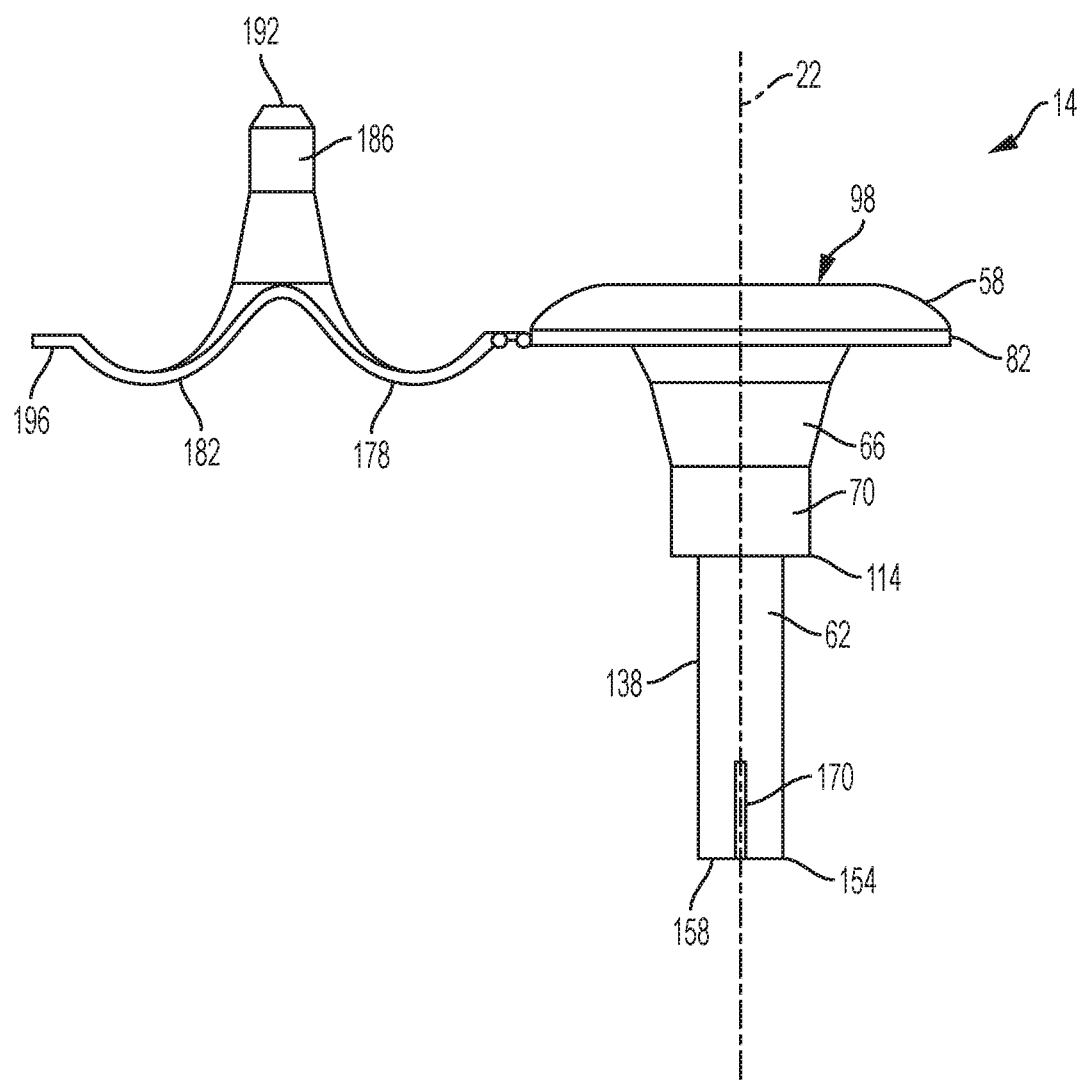
FIG. 7 is a side view of the filter device of the sample collection device of FIG. 1 with the lid in an open position.
Figure 8:
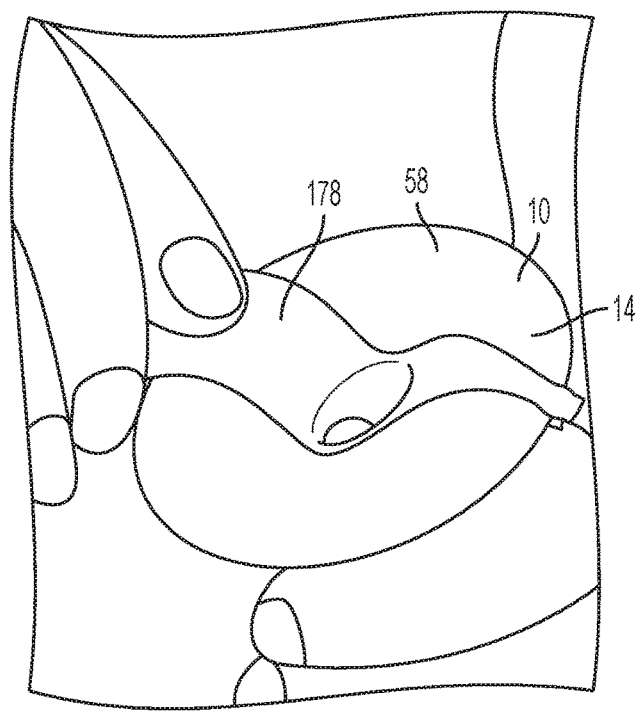
FIG. 8 illustrates a fully assembled sample collection device with the lid in a closed position.
Figure 9:
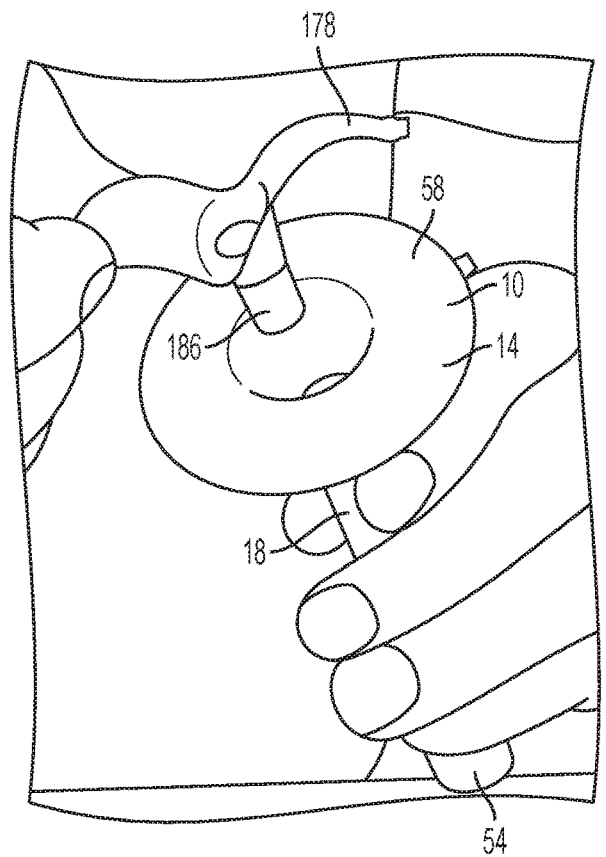
FIG. 9 illustrates the sample collection device of FIG. 8, with the lid moved to an open position by the user.
Figure 10:
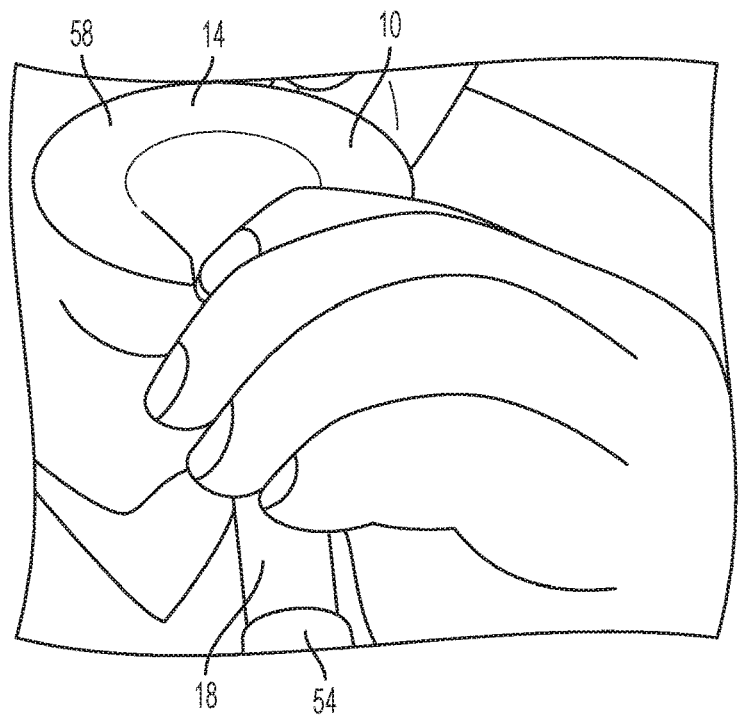
FIG. 10 illustrates a user depositing a sample into the sample collection device of FIG. 8.
Figure 11:
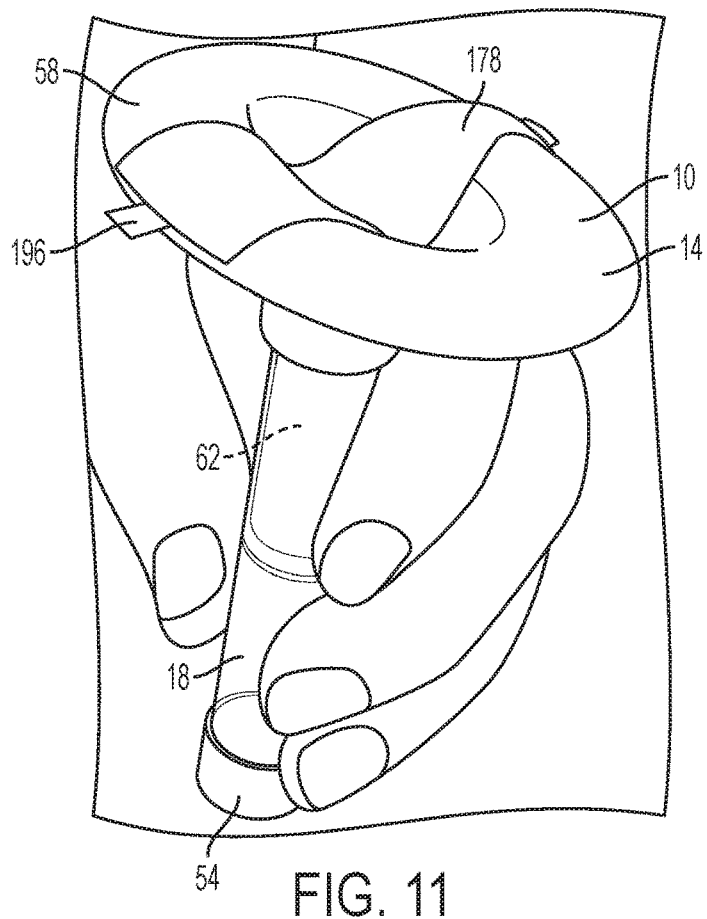
FIG. 11 illustrates the sample collection device of FIG. 8 with a sample deposited therein and the lid returned to the closed position.

Illustrated in FIGS. 5-7, the filter 62 of the filtering device 14 is substantially cylindrical in shape having an outer annular wall 138 defining a channel 146 therethrough. The annular wall 138, in turn, includes a first or open end 150 that provides access to the channel 146, and a second end 154 opposite the open end 150 that is enclosed by a perforated wall 158. During use, the sample enters the channel 146 of the filter 62 via the open end 150, travels along the axial length of the channel 146, and exits the filter 62 through the perforated wall 158. In some embodiments, the annular wall 138 may be sufficiently long so that elongated items, such as swabs, can be positioned within the channel 146 of the filter 62 during use while leaving sufficient space for a cap or lid (described below) to be used.

In the illustrated embodiment, the open end 150 of the filter 62 includes a ridge 162 extending radially outwardly from the annular wall 138. During use, the ridge 162 is configured to be at least partially received within and engage the second portion 126 of the channel 74. More specifically, the ridge 162 is substantially oval-shaped having two opposing lobes that are configured to contact corresponding recesses of the second portion 126 of the mouthpiece 58 to stop the filter 62 from completely passing axially through the channel 74 of the neck 70. In some embodiments, the ridge 162 may also include a gasket or other geometry allowing the ridge 162 to form a seal with the second portion 126 of the channel 74, thereby limiting any spillage and assuring the entire sample introduced into the mouthpiece 58 is ultimately directed into and passes through the filter 62.

Best illustrated in FIG. 6, the perforated wall 158 of the filter 62 substantially encloses the second end 154 of the annular wall 138. The perforated wall 158 defines a plurality of apertures 166 sized large enough to allow the sample and stabilizing agent to flow therethrough, yet sufficiently small to restrict the passage of any debris or particles. In the illustrated embodiment, each aperture 166 of the perforated wall 158 is substantially rectangular in shape and includes an "effective width" defined herein as the shortest width produced by the aperture 166. While the illustrated apertures 166 are rectangular in shape, the apertures 166 may include any cross-sectional shape such as circular, oval, polygonal, and the like.

In the illustrated embodiment, the apertures 166 of the perforated wall 158 are arranged in a substantially rectangular array, being positioned generally evenly over the entire wall 158. In alternative embodiments, the apertures 166 may be oriented in a radial array, or be positioned in other orientations that produce the necessary filtering attributes. The illustrated perforated wall 158 is also substantially planar in contour, defining a filter plane 174 on which each of the apertures 166 are positioned. In alternative embodiments, the perforated wall 158 may be semi-circular, conical, and the like.

It is to be understood that while the perforated wall 158 of the present invention is integrally formed with the annular wall 138 of the filter 62, in alternative embodiments the perforated wall 158 may be formed separately and be removably coupled thereto.

The filter 62 also defines one or more by-pass apertures 170 formed into the annular wall 138 and configured to permit the stabilizing buffer to flow behind and completely encompass the sample when it is positioned within the channel 146 of the filter 62. As shown in FIG. 7, the by-pass apertures 170 are oriented such that at least a portion of the apertures 170 are positioned behind or upstream of the perforated wall 158. Stated differently, at least a portion of the by-pass apertures 170 are positioned axially offset from and behind the filter plane 174 (e.g., closer to the open end 150 of the filter 62). In the illustrated embodiment, each by-pass aperture 170 includes an elongated slot originating proximate the second end 154 and extending axially along the annular wall 138 toward the open end 150. However, in alternative embodiments, the by-pass apertures 170 may include a circular or rectangular aperture formed in the annular wall 138 and displaced axially from the perforated wall 158. In the illustrated embodiment, the by-pass apertures 170 have an effective width that is less than or equal to the effective width of the apertures 166 formed in the perforated wall 158.

While the filter 62 is shown as being separate from the mouthpiece 58, it is to be understood that in alternative embodiments the two elements may be formed together as an integral unit. Furthermore, the filter 62 may be one of multiple, interchangeable filters, each having a unique aperture size and layout corresponding to the specific types and sizes of debris it is intended to filter out or allow therethrough.

Illustrated in FIGS. 1-4, and 6-13, the filtering device 14 also includes a cap or lid 178 to selectively seal the open end 150 of the filter 62. The lid 178 includes a base portion 182 and a sealing projection 186 extending from the base portion 182 to form a distal end 192. During use, the lid 178 is movable with respect to the filtering device 14 between a closed position, where at least a portion of the projection 186 is positioned within channel 146 to restricts access thereto (see FIGS. 1, 4, 6, and 8), and an open position, where the projection 186 is not positioned within and does not restrict access to the channel 146 of the filter 62 (see FIGS. 2, 3, 7, and 9)

The base portion 182 of the lid 178 is shaped to substantially correspond with the contour of the outer surface 98 of the mouthpiece 58. The base portion 182 also includes a tab or handle 196 extending from the base portion 182 beyond the outer perimeter 82 of the mouthpiece 58 such that the user may grasp the tab 196 and manipulate the lid 178 between the open and closed positions. The base portion 182 may also include a lanyard or flexible connection 200 extending between the base portion 182 and the mouthpiece 58 to couple the two items together.

Figure 13:
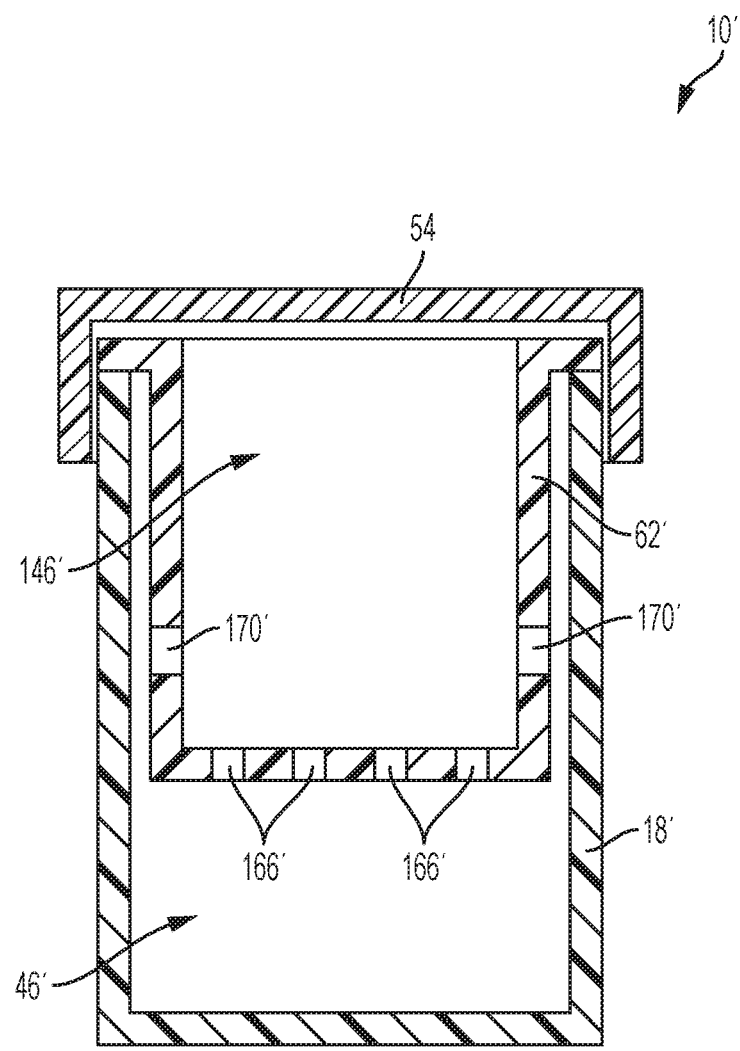
FIG. 13 is a cross-section view of another embodiment of the sample collection device.

Illustrated in FIG. 13, the device 10 also includes a travel cap 54 removably couplable to both the first end 30 and the second end 34 of the collection tube 18. The travel cap 54 includes a set of internal threads (not shown) sized to engage the external threads 50 of the first end 30 of the collection tube 18, and a groove (not shown) sized to releasably receive at least a portion of the second end 34 of the collection tube 18. The travel cap 54 may also include a set of bar codes or other identifying indicia printed thereon (not shown).

To pre-assemble the filtering device 14, the user combines the filter 62 and the mouthpiece 58. To do so, the user axially inserts the second end 154 of the filter 62 into the channel 74 of the mouthpiece 58. The user continues to advance the filter 62 into the channel 74 until the ridge 162 of the open end 150 of the filter 62 engages with and is seated within the second portion 126 of the channel 74 forming a seal therebetween (see FIG. 7).

Once assembled, the user may then install the filtering device 14 on a sample collection tube 18. To do so, the user first removes the travel cap 54 from the collection tube 18 exposing the external threads 50 thereof and providing access to the storage volume 46 via the first end 30. The user then stows the travel cap 54 by attaching it to the second end 34 of the collection tube 18 by inserting at least a portion of the second end 34 into the corresponding groove of the travel cap 54 (see position of travel cap 54 in FIG. 12).

With the travel cap 54 removed and stowed, the user may then couple the assembled filtering device 14 to the collection tube 18. The user does so by inserting the second end 154 of the filter 62 into the storage volume 46 and screwing the internal threads 130 of mouthpiece 58 to the external threads 50 of the collection tube 18. Once completed, the mouthpiece 58 forms a seal with the collection tube 18 such that the storage volume 46 may only be accessed via the channel 146 of the filter 62. As such, any fluids or samples must pass through the filter 62 (e.g., the apertures 166 of the perforated wall 158) in order to enter or exit the storage volume 46 (see FIG. 6).

In some embodiments, a pre-measured volume of stabilizing buffer may be placed in the storage volume 46 via the channel 146 of the filter 62 or directly into the first end 30 before the filtering device 14 and the collection tube 18 are coupled together. However, in alternative embodiments, the stabilizing buffer may come pre-loaded in the storage volume 46.

In instances where the collection device 10 is not intended to be used immediately, the user may position the lid 178 of the mouthpiece 58 in the closed position, sealing the open end 150 of the channel 146, and as a result, restricting access to the storage volume 46.

To collect a sample, the user first re-orients the lid 178 from the closed position (see FIG. 8), to the open position (see FIG. 9), thereby providing access to the storage volume 46 via the channel 146 of the filter 62. Once opened, the user places his or her lips against the outer surface 98 of the mouthpiece 58 and spits until the necessary volume of sample is produced (e.g., approximately three times; see FIG. 11). As described above, the shape and contour of the mouthpiece directs the resulting sample toward the open end 150 of the filter 62 and into the channel 146 thereof. The sample then travels along the channel 146 and contacts the perforated wall 158.

Figure 12:
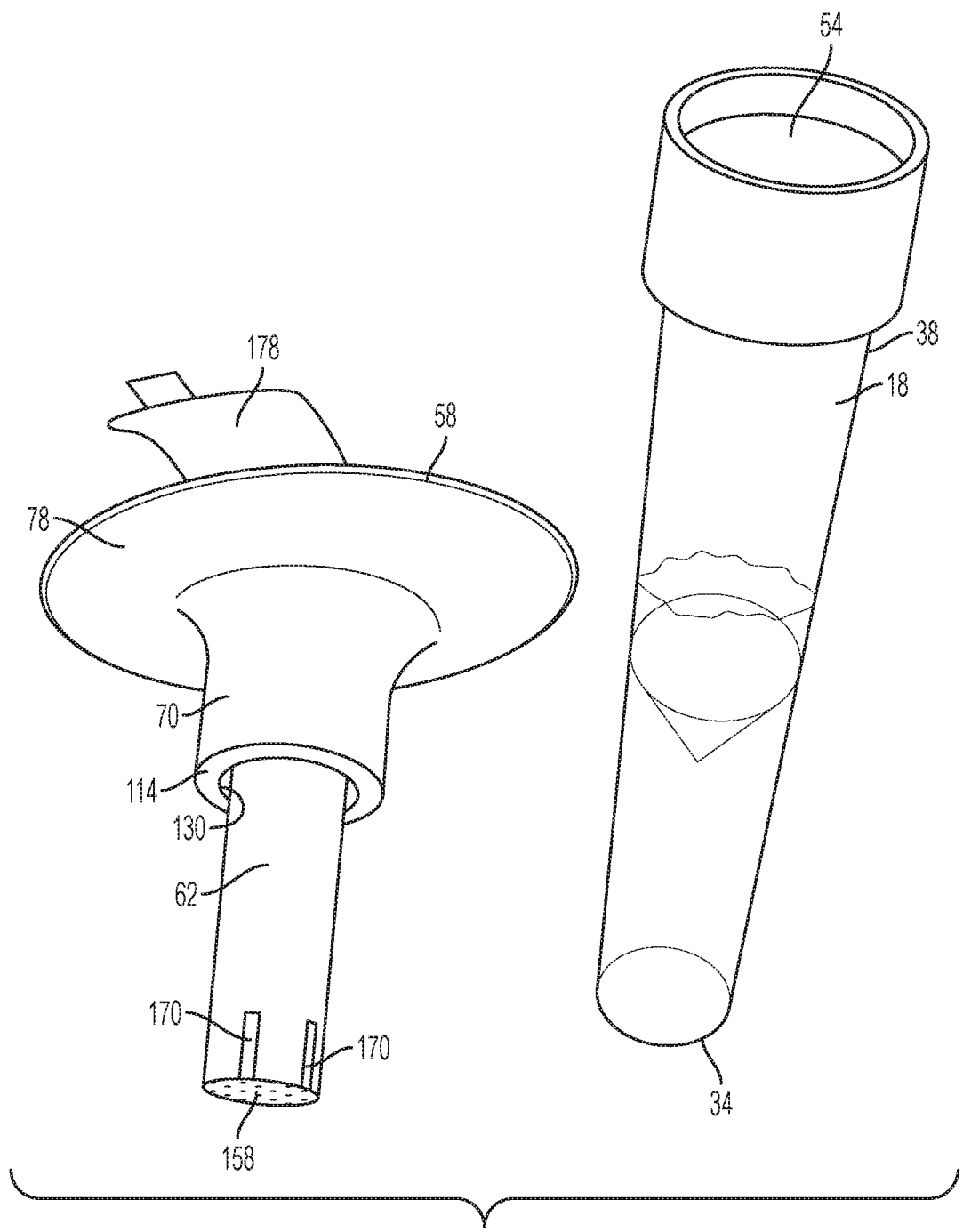
FIG. 12 illustrates the sample collection device of FIG. 8 with the filtering device removed from the collection tube and the travel cap positioned on the collection tube.

With the sample deposited within the filter 62, the user then closes the device 10 by replacing the lid 178 to the closed position (see FIG. 12). By doing so, the user seals the open end 150 of the filter 62 and produces an isolated volume 208 within the device 10 that includes the storage volume 46 of the collection tube 18 and the channel 146 of the filter 62.

Once closed, the user agitates the device until the stabilizing buffer and the sample are thoroughly mixed (e.g., shaking the device approximately 10 times). When agitating the device 10, the agitation motion causes the stabilizing buffer and sample to slosh around within the isolated volume 208. More specifically, the stabilizing buffer flows through both the apertures 166 of the perforated wall 158 and the by-pass apertures 170 contacting and mixing with all sides of the generally more viscous oral sample. Simultaneously, the sample itself is forced through the apertures 166 of the perforated wall 158 causing all contaminants and particles larger than the effective width of the apertures 166 to be removed therefrom. Once complete, the agitation results in a mixed and filtered sample positioned in the bottom of the storage volume 46 of the sample tube 18 and all particulates and other containments remaining positioned within the channel 146 of the filter 62.

With the sample prepared, the user may then store or ship the device for future processing and testing. In some instances, the user may remove the filtering device 14 from the collection tube 18 by un-screwing the mouthpiece 58 therefrom. By doing so, the user removes the debris and other particles positioned within the channel 146 of the filter 62 from the storage volume 46—leaving only the mixed stabilizing buffer and sample solution behind. The user can then re-thread the travel cap 54 onto the first end 30, sealing the storage volume 46 for travel and storage (see FIG. 12).

FIG. 13 illustrates an alternative embodiment of the sample collection device 10'. The sample collection device 10' is substantially similar to the sample collection device 10 and therefore only the differences are described herein. The sample collection device 10' includes a collection tube 18' and a filter 62' removably coupled to the collection tube 18' directly without a mouthpiece 58 present. In such an embodiment, the lack of a mouthpiece 58 reduces the device's footprint allowing the device 10' to be more easily stored and handled. Such embodiments are typically used in conjunction with swabs, cotton balls, filter paper, and the like where the enlarged entry area of the mouthpiece 58 is not necessarily needed. Furthermore, the filter 62' may be sized and shaped such that the travel cap 54 may completely encompass and seal the storage volume 46' with the filter 62' positioned therein.

Although the invention has been described in detail with reference to certain preferred embodiments, variations and modifications exist within the scope and spirit of one or more independent aspects of the invention as described.

The invention claimed is:

1. A sample collection device comprising:
 a collection tube at least partially defining a storage volume therein;
 a mouthpiece coupled to the collection tube, the mouthpiece defining a channel providing access to the storage volume; and
 a filter at least partially positioned within the channel, the filter comprises a perforated wall defining a plurality of apertures, and wherein the filter forms a flow path between the storage volume and the channel.

2. The sample collection device of claim 1, wherein the storage volume includes a volume of stabilizing buffer therein.

3. The sample collection device of claim 1, wherein the mouthpiece is substantially conical in shape.

4. The sample collection device of claim 1, wherein the mouthpiece defines an oval-shaped outer perimeter.

5. The sample collection device of claim 4, wherein the collection tube defines an axis, and wherein the mouthpiece produces a minimum rest angle greater than approximately 10 degrees when measured from an angle between a first ray originating at a base of the collection tube and running along the exterior thereof in a direction parallel to the axis and a second ray originating from the same point as the first ray intersecting the outer perimeter of the mouthpiece.

6. The sample collection device of claim 1, wherein the filter is formed separately from the mouthpiece.

7. The sample collection device of claim 1, wherein the filter further includes an inlet and one or more by-pass apertures positioned closer to the inlet than the perforated wall.

8. The sample collection device of claim 7, wherein the one or more by-pass apertures define a first effective width, and wherein the plurality of apertures define a second effective width, and wherein the first effective width is smaller than or equal to the second effective width.

9. The sample collection device of claim 1, where at least one of the plurality of apertures are substantially rectangular in shape.

10. A filtering device for use with a collection tube defining a storage volume therein, the filtering device comprising:
   a mouthpiece being substantially conical in shape and defining a channel configured to allow a sample to flow therethrough; and
   a filter at least partially positioned within the channel, wherein the filter defines a plurality of apertures configured to filter a sample passing through the channel, and wherein when the filtering device is coupled to a collection tube the filter forms a flow path between the storage volume and the channel.

11. The filtering device of claim 10, wherein the plurality of apertures are rectangular in shape.

12. The filtering device of claim 10, wherein the plurality of apertures are positioned in a rectangular array.

13. The filtering device of claim 10, wherein the filter also defines an inlet and one or more by-pass apertures positioned closer to the inlet than the plurality of apertures.

14. The filtering device of claim 10, wherein the mouthpiece includes a substantially oval-shaped outer perimeter.

15. A filtering device for use with a collection tube defining a storage volume therein, the filtering device comprising:
   a channel having a first end, and a second end opposite the first end;
   a mouthpiece extending from the channel proximate the first end, wherein the mouthpiece is substantially conical in shape; and
   a perforated wall enclosing the second end of the channel, wherein the perforated wall defines a plurality of apertures therein.

16. The filtering device of claim 15, wherein the mouthpiece and the channel are formed separately.

17. The filtering device of claim 15, wherein the perforated wall and the channel are formed separately.

18. The filtering device of claim 15, further comprising one of more by-pass apertures closer toward the first end of the channel than the perforated wall.

19. The filtering device of claim 18, wherein the second end of the channel includes an end wall and at least one side wall extending from the perimeter of the end wall, and wherein the end wall defines the perforated wall, and wherein the side wall defines the one or more by-pass apertures.

20. A sample collection device comprising:
   a collection tube at least partially defining a storage volume therein;
   a filter positioned at least partially within the collection tube and configured to subdivide the storage volume into a first portion and a second portion, the filter including a first, open end, and a second end opposite the open end, where the second end includes an end wall and at least one side wall extending from the end wall toward the first end, wherein the end wall defines a first plurality of apertures defining a second effective width, and wherein the side wall defines a second plurality of by-pass apertures defining a first effective width, wherein the first effective width is smaller than the second effective width, and wherein each aperture of the first plurality of apertures and each aperture of the second plurality of apertures extend between and are in fluid communication with both the first portion and the second portion of the storage volume.

21. The sample collection device of claim 20, further comprising a mouthpiece coupled to the collection tube proximate the first end of the filter, the mouthpiece defining a channel providing access to the storage volume via the filter.

22. The sample collection device of claim 20, wherein the collection tube is configured to house a stabilizing buffer within the storage volume.

23. The sample collection device of claim 20, wherein the plurality of apertures are rectangular in shape.

24. The sample collection device of claim 20, wherein the plurality of apertures are positioned in a rectangular array.

25. A sample collection device comprising:
   a collection tube at least partially defining a storage volume therein;
   an insert positioned at least partially within the collection tube and configured to subdivide the storage volume into a first portion and a second portion, wherein the insert defines:
      one or more first apertures defining a first effective width, wherein each first aperture extends between and is in fluid communication with both the first portion and the second portion of the storage volume, and
      one or more second apertures defining a second effective width, wherein the first effective width is larger than the second effective width, and wherein each second aperture extends between and is in fluid communication with both the first portion and the second portion of the storage volume.

26. The sample collection device of claim 25, wherein the collection tube defines an inlet providing external access to the storage volume, and wherein the first portion of the storage volume is accessible via the inlet.

27. The sample collection device of claim 26, further comprising a cap to selectively seal the inlet of the collection tube.

28. The sample collection device of claim 25, wherein the one or more second apertures are bypass apertures configured to permit fluid to flow between the first portion and the second portion of the storage volume.

29. The sample collection device of claim 28, wherein the storage volume includes a pre-measured volume of stabilizing buffer contained therein.

30. The sample collection device of claim 25, wherein the one or more second apertures are any one of circular, oval, polygonal, and rectangular in cross-sectional shape.

31. The sample collection device of claim 25, wherein the one or more first apertures are any one of circular, oval, polygonal, and rectangular in cross-sectional shape.

32. The sample collection device of claim 25, wherein the collection tube defines an axis therethrough, and wherein at least a portion of the insert is oriented normal to the axis.

33. The sample collection device of claim 32, wherein the one or more first apertures are formed in the at least portion of the insert that is oriented normal to the axis.

34. The sample collection device of claim 33, wherein the one or more second apertures are formed in the at least portion of the insert that is oriented normal to the axis.

35. The sample collection device of claim 32, wherein the one or more second apertures are formed in the at least portion of the insert that is oriented normal to the axis.

* * * * *